United States Patent [19]
Marino

[11] Patent Number: 6,132,378
[45] Date of Patent: Oct. 17, 2000

[54] COVER FOR ULTRASOUND PROBE

[76] Inventor: Sharon Marino, 4311 Summit St., Pittsburgh, Pa. 15201

[21] Appl. No.: 09/131,612

[22] Filed: Aug. 10, 1998

[51] Int. Cl.[7] .................................................. A61B 8/00
[52] U.S. Cl. ............................................... 600/459
[58] Field of Search ..................... 600/459, 437, 600/458, 460, 461; 428/35.2

[56]   References Cited

U.S. PATENT DOCUMENTS

| 4,796,632 | 1/1989 | Boyd et al. | 600/437 |
| 4,867,169 | 9/1989 | Machida et al. | 600/459 |
| 4,887,615 | 12/1989 | Taylor . | |
| 5,265,614 | 11/1993 | Hayakawa et al. . | |
| 5,655,539 | 8/1997 | Wang et al. . | |
| 5,676,159 | 10/1997 | Navis | 600/437 |
| 5,775,328 | 7/1998 | Lowe et al. | 600/459 |
| 5,795,632 | 8/1998 | Buchalter | 428/35.2 |

*Primary Examiner*—Marvin M. Lateef
*Assistant Examiner*—Maulin Patel
*Attorney, Agent, or Firm*—Buchanan Ingersoll, P.C.

[57]   ABSTRACT

A cover for an ultrasound probe is cup shaped and has an opening in the cup base. The cover is configured to fit onto the probe and maintain the cover on the probe with the cup base being a selected distance from the probe base to define a volume between the probe base and the cup base. A pliable, sound conductive membrane is attached to the cup adjacent the base and covers the opening. The membrane is sized to substantially fill the volume between the probe base and the cup base so that when the cup is attached to the ultrasound probe the probe base will be in contact with the membrane. The membrane is sufficiently pliable such that when placed on a portion of the human body the membrane will conform to that portion of a human body against which the membrane is placed.

10 Claims, 2 Drawing Sheets

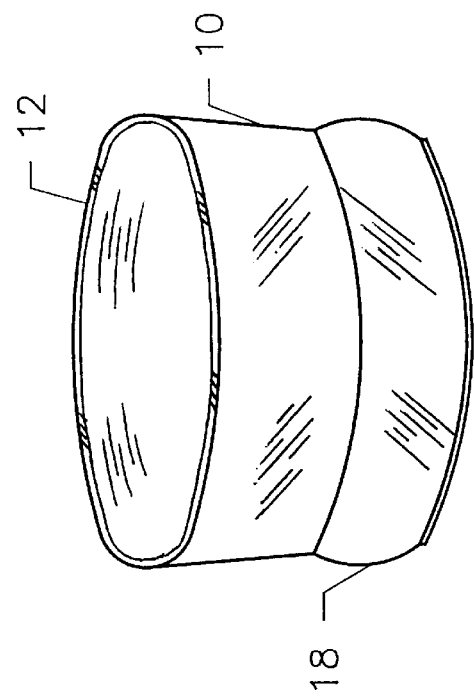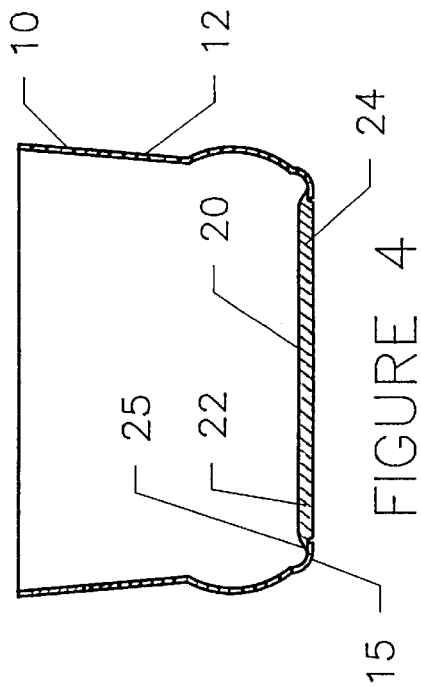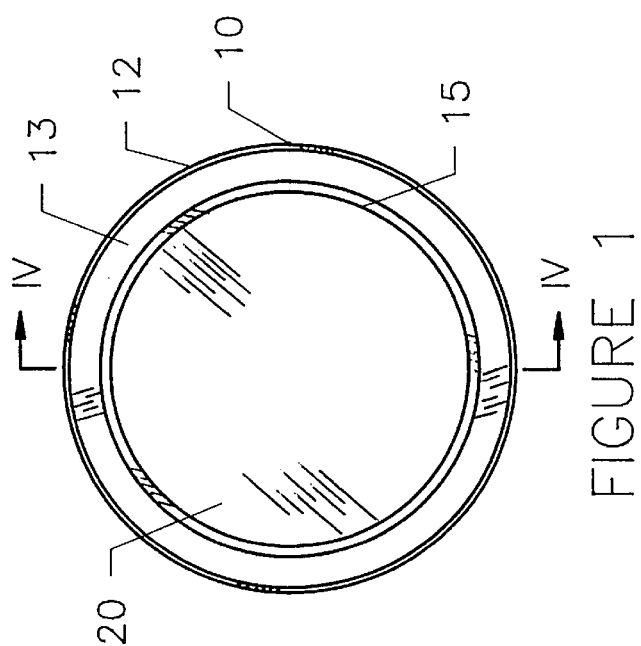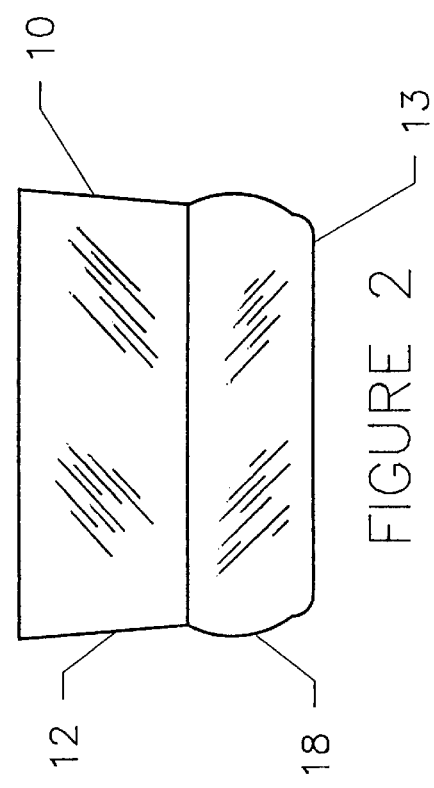

COVER FOR ULTRASOUND PROBE

BACKGROUND OF THE INVENTION

The invention relates to covers for an ultrasound head or probe which is used for diagnosis or treatment of the human body.

DESCRIPTION OF THE PRIOR ART

For many years ultrasound has been used for diagnosis and treatment of a variety of conditions in the human body. In these procedures a probe is provided which transmits ultrasound waves into the body. Reflected waves are detected and used to create images of a portion of the human body. Some ultrasound probes can be inserted into body cavities or incisions. Other probes are placed on the surface of the skin. When these non-invasive probes are used it is necessary to provide an acoustic coupler between the probe and skin. One common procedure is to simply apply gel to the surface of the skin and press the probe into the gel. This procedure has several disadvantages. First, the gels typically cannot be used over wounds. Second, the procedure is messy. Gel must be cleaned from the patient and the probe after the procedure has been completed. Third, if the probe is pressed too hard against the skin the gel may be squeezed from the region between the probe and the skin. Fourth, air bubbles or air pockets can be present between the probe and the gel and between the gel and the skin. If air bubbles are present or a gel escapes from between the skin and the probe, artifacts may appear in the image which is generated. These artifacts have been known to lead to an incorrect medical diagnosis. There have been occasions when an ultrasound image has shown what appeared to be a tumor in a patient. However, when surgery was performed no tumor was found.

There are some therapeutic treatments in which the ultrasound probe must be over a region of the body which is larger than the diameter of the probe such as a shoulder. If a gel is used, it is necessary to cover the entire shoulder or other region of interest with the gel and move the probe through the gel. It is much more likely that in this procedure air bubbles will appear or gel will be squeezed away from the skin.

There are now available covers made of latex or flexible polyurethane which are similar to a balloon and contain a sound conducting gel. One example of this type of product is disclosed in U.S. Pat. No. 5,676,159 to Navis. That cover is essentially a flat plastic bag with gel repositioned in the closed end of the bag. The bag is placed over the end of the probe and secured. However, as the probe is moved the gel will dislocate. Also, the bag cannot conform to the shape of the ultrasound probe. After this occurs the probe will be unable to distinguish skin or tissue variations. Typically these bags are intended for a single patient use as they must be sterile. When the bag is removed from the probe gel will adhere to the end of the probe. Consequently, the probe must be cleaned before it can be used again.

U.S. Pat. No. 5,655,539 discloses an ultrasound procedure in which an ultrasound transmissive pad is placed on the patient. The pad includes a first layer having a porous portion and a second layer also having pores therethrough. The second layer is attached to the first layer so as to define a space therebetween. An ultrasound couplance is disposed in that space. Although the pad prevents the couplance from adhering to either the patient or the probe, the pad has other shortcomings. In many procedures the physician or medical technician will move the probe over an area of the human body while observing an image created on a monitor. Thus, the pad must either be large enough to cover the entire area or be moved with the probe. Since the pad is not attached to either the probe or the patient it may shift as the probe is being moved. In order to move the pad with the probe the user must hold the probe with one hand and the pad with the other. This quite cumbersome and may make it difficult for the physician to observe the monitor. Another sterile drape for an ultrasound probe is disclosed in U.S. Pat. No. 4,887,615 to Taylor. This drape is an elongated sleeve which fits around the end of the probe. The drape contains a conductive gel. Although the drape can be moved with the probe it is difficult to ensure that the drape remains in place during the procedure.

Another acoustic coupler is disclosed in U.S. Pat. No. 5,265,614. A primary purpose of the coupler is to function as an acoustic standoff pad for raising the ultrasound probe a selected distance from the surface to be acoustically inspected. This coupler is made of a gel, part of which is hardened around the probe. This coupler has the advantage of being connected to the probe and easily moved. However, it is difficult to remove this type of coupler from the probe and to repeatedly sterilize it. The coupler is made by molding a polyvinyl alcohol solution so that the upper part which grips the probe is hardened to a greater extent than the lower portion through which ultrasound waves are directed. There is no teaching that the lower portion is flexible enough to conform to irregular surfaces such as a human hand. Furthermore, the gelled material tends to dry up and must be stored or immersed in a liquid before use.

Consequently, there is a need for a cover for ultrasonic probes which can easily be attached to and removed from the probe. The cover should not require special storage and should be easily sterilized. Furthermore, the cover should provide an acoustic coupling between the probe and the skin so as to eliminate artifacts in the image produced.

SUMMARY OF THE INVENTION

I provide a cover for an ultrasound probe which is a cup-like device that fits over the probe. When attached to the probe the base of the cup will be a selected distance from the base of the probe. An opening is provided in the base of the cup. A pliable sound conducting membrane is attached to the cup adjacent its base and covers the opening. The membrane is sized to substantially fill the volume between the probe and the cup base so that when the cup is attached to the ultrasound probe the probe base will be in contact with the membrane. The membrane is sufficiently pliable so that when placed on a portion of the human body, the membrane will conform to that portion of the human body against which the membrane is placed. The membrane preferably is comprised of two polyurethane sheets sealed at their edges to form a cavity. Water or other sound conducting material fills the cavity. This cover can be readily attached to and removed from an ultrasound probe. When removed the cover can be sterilized. Furthermore, the cover is made of inexpensive materials and as such is disposable.

Other objects and advantages of the present invention will become apparent from the description of certain present preferred embodiments shown in the drawings.

BRIEF DESCRIPTION OF THE FIGURES

FIG. 1 is a top plan view of a first present preferred embodiment of my cover.

FIG. 2 is a side view thereof.

FIG. 3 is a perspective view of the embodiment shown in FIGS. 1 and 2.

FIG. 4 is a cross section of a view taken along the line IV—IV of FIG. 1 showing the cover placed on a probe which is not sectioned.

DETAILED DESCRIPTION OF THE INVENTION

Figure 6:
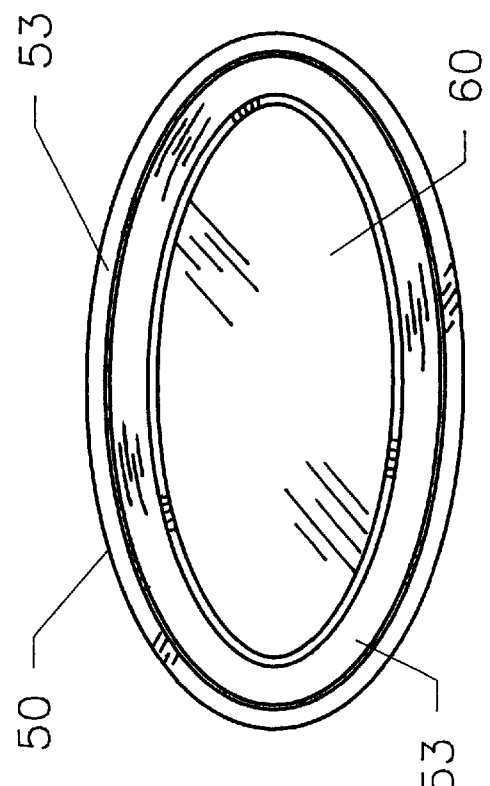
FIG. 6 is a top plan view of a second preferred embodiment of my cover.

My cover 10 for an ultrasound probe has a flexible cup-shaped body 12 with the center of the bottom 13 removed to form an opening 16. A flexible liquid or gel filled membrane 20 is permanently fixed to the inside bottom. I prefer to fill the membrane with water. However, water based gels, mineral oil, oil based gels, glycerin, vegetable oil or liquid paraffin could be used. The cover 10 is configured to snap onto the ultrasound head or probe 30 shown in FIG. 5 to a position where the sound transmissive base 32 of the probe is always in contact with the liquid or gel filled membrane. The cover may or may not be sterilized given the application. The liquid or gel filled membrane is affixed to the cover 10 at a location 15 in the inside bottom by heat sealing or bonding the edges. Once the probe or head is inserted into the cover, the sound transmitting base of the probe or head is fully contacting the flexible membrane 20.

Most of the ultrasound probes that are used for non-invasive procedures have a collar 34 adjacent the sound conducting base 32 of the probe 30. The probes are cylindrical and have a circular or oval cross-section. The first embodiment of my cover 10 shown in FIGS. 1 through 5 is sized for use on a circular cylindrical probe and the second embodiment shown in FIG. 6 is shaped for use on an oval cylindrical probe. I provide an outward bulge 18 adjacent the base 13 of the body. This bulge is sized to fit over the collar 32 on the probe 30. Because the body 12 is made of a flexible material, the cover 10 will snap onto the ultrasound head or probe and remain in place until pulled away from the probe. Consequently, the cover 10 can be quickly attached to and removed from the probe. Since the gel is contained within a membrane the probe need not be cleaned between use. Rather, the used cover is removed and a second sterilized cover is placed on the probe.

The body 12 of cover 10 can be vacuum formed or injection molded preferably from polyurethane or polyvinyl chloride. It can be made to the desired size and thickness to fit various ultrasound heads or probes. This thickness should range from 4 to 120 mils (0.040 inch to 0.120 inch). The optimal thickness may be different for different probes and materials. That thickness can be determined for each specific ultrasound head or probe. The flexible membrane 20 is constructed by entrapping gel or liquid 24 between two thin polyurethane sheets 22 and heat sealing or bonding the sides 25 of the membrane 20 to the desired shape of the membrane. The polyurethane sheets 22 preferably have a thickness of 1 to 7 mils (0.001 to 0.007 inch). A commercially available source of suitable polyurethane sheet material is Deerfield Urethane Inc.

Figure 5:
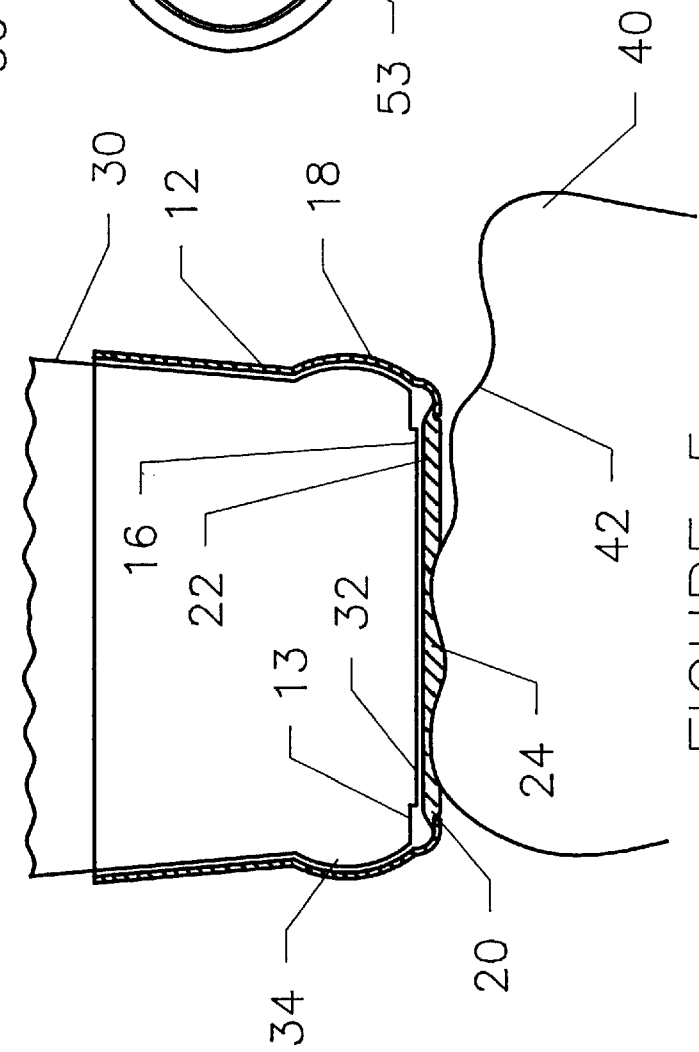
FIG. 5 is a sectional view showing the probe and cover placed on a portion of the skin.

As can be seen in FIG. 5 the gel or liquid filled membrane is sufficiently flexible to enable the probe cover 10 to conform to the region of the human body over which it is placed. In that figure the membrane 20 is shown as being placed over a fist 40 and conforming to the knuckles 42. Because the sound transmissive gel or liquid is within the membrane, the probe cover can be placed over a wound without any gel or liquid entering the wound.

The art has added certain medications to acoustic coupling gels which are placed on the skin. There is some evidence that the application of ultrasound through the medicated gel causes the medicine to penetrate more deeply into the tissue being treated. This same benefit can be obtained by applying the medicine over the skin and placing the ultrasound probe cover over the medicine. If this practice were followed to treat the knuckles in a human hand then the medicine would be between membrane 20 and the skin over knuckles 42 shown in FIG. 5. Hydrocortisone cream is one medicine that could be applied in this manner. In another treatment antibiotic creams are applied over a wound and then the wound is treated with ultrasound using a probe having the probe cover disclosed herein.

A second preferred cover 50 is shown in FIG. 6. The embodiment for the cover 10 shown in FIG. 1 is similar to cover 50 in FIG. 6, except that the body 52 is oval shaped to fit a different type of probe. An oval membrane 60 fits on the base 53 and covers an opening in the base as in the first embodiment. Since this type of probe also has a collar, the body 52 has a bulge 58 to enable the cover 50 to snap onto the probe.

The exact dimensions or proportions of the preferred embodiment and the alternate embodiments are not critical to the invention. The suppleness, structure, and size of the cover can be made to the dimensions required for a particular probe. It will also be appreciated that although the invention has been disclosed with reference to certain probes, it encompasses a cover for similar instruments of different sizes and shapes. Further, an entire family of ultrasound covers can be produced for all types of ultrasound probes.

Because the covers are configured to snap fit onto the probe and contain the sound conducting liquid or gel within a membrane, they can be quickly attached to and removed from a probe. No time need be spent in cleaning liquid or gel from the patient or the probe. The cover can be made from inexpensive materials that are already commonly used in medical equipment which contacts a patient's skin. The covers can be disposable or sterilized again for multiple patient use. There should be no concerns about adverse patient skin reactions or extensive clinic trials or dermatology testing before this product can be used.

Although I have shown and described certain present preferred embodiments of my cover for an ultrasound probe, it should be distinctly understood that the invention is not limited thereto but may be variously embodied within the scope of the following claims.

I claim:

1. A cover for an ultrasound probe, the probe having a probe base through which sound waves are transmitted, a probe wall extending from the base and an exterior collar on the probe wall adjacent the probe base, the cover comprising:

a. a cup having a cup base which has an opening and a cup wall extending from the cup base, the cup wall configured to fit around the probe wall and snap over the collar to maintain the cup on the probe with the base being a selected distance from the probe base to define a volume between the probe base and the cup base; and b. a pliable, sound conductive membrane attached to the cup adjacent the base and covering the opening, the membrane having two layers bonded together to form a fully enclosed cavity, the membrane sized to substantially fill the volume between the probe base and the cup base so that when the cup is attached to the ultrasound probe the probe base will be in contact with the membrane, the membrane being sufficiently pliable such that when placed on a portion of the human body the membrane will conform to that portion of a human body against which the membrane is placed.

2. The cover of claim 1 wherein the cavity is filled with a material selected from the group consisting of water, water based gels, oil, oil based gels, glycerin, vegetable oil and liquid paraffin.

3. The cover of claim 1 wherein the membrane is comprised of polyurethane sheets sealed together at their edges to form the cavity.

4. The cover of claim 3 wherein the polyurethane sheets have a thickness of from 1 to 7 mils.

5. The cover of claim 1 wherein the membrane is attached to the cup by a heat seal.

6. A cover for an ultrasound probe of the type having a probe base through which sound waves are transmitted comprising:

a. a cup having a cup base which has an opening and a cup wall extending from the cup base, the cup configured to fit onto the probe and maintain the cup on the probe with the base being a selected distance from the probe base to define a volume between the probe base and the cup base; and b. a pliable, sound conductive membrane attached to the cup adjacent the base and covering the opening, the membrane having two layers bonded together to form a fully enclosed cavity, the membrane sized to substantially fill the volume between the probe base and the cup base so that when the cup is attached to the ultrasound probe the probe base will be in contact with the membrane, the membrane being sufficiently pliable such that when placed on a portion of the human body the membrane will conform to that portion of a human body against which the membrane is placed.

7. The cover of claim 6 wherein the cavity is filled with a material selected from the group consisting of water, water based gels, oil, oil based gels, glycerin, vegetable oil and liquid paraffin.

8. The cover of claim 6 wherein the membrane is comprised of polyurethane sheets sealed together at their edges to form the cavity.

9. The cover of claim 8 wherein the polyurethane sheets have a thickness of from 1 to 7 mils.

10. The cover of claim 6 wherein the membrane is attached to the cup by a heat seal.

* * * * *